(12) United States Patent
Shimoji et al.

(10) Patent No.: US 8,177,797 B2
(45) Date of Patent: May 15, 2012

(54) SUTURE REINFOREMENT MATERIAL FOR AUTOMATIC SUTURING DEVICE

(75) Inventors: Hiroyuki Shimoji, Ayabe (JP); Hitoshi Ohtani, Ayabe (JP)

(73) Assignee: Gunze Limited, Kyoto (JP)

( * ) Notice: Subject to any disclaimer, the term of this patent is extended or adjusted under 35 U.S.C. 154(b) by 696 days.

(21) Appl. No.: 10/564,874

(22) PCT Filed: Jul. 16, 2004

(86) PCT No.: PCT/JP2004/010566
§ 371 (c)(1),
(2), (4) Date: Jan. 17, 2006

(87) PCT Pub. No.: WO2005/007208
PCT Pub. Date: Jan. 27, 2005

(65) Prior Publication Data
US 2006/0178683 A1 Aug. 10, 2006
US 2007/0049953 A2 Mar. 1, 2007

(30) Foreign Application Priority Data
Jul. 17, 2003 (JP) ................................. 2003-198240

(51) Int. Cl.
*A61B 17/08* (2006.01)
(52) U.S. Cl. ...................................................... 606/151
(58) Field of Classification Search .................. 606/151, 606/139, 228; 112/22, 438; 383/79, 92; 289/1.2, 1.5, 17
See application file for complete search history.

(56) References Cited

U.S. PATENT DOCUMENTS

| | | | | |
|---|---|---|---|---|
| 1,164,451 A | * | 12/1915 | Bates | 383/121 |
| 2,259,025 A | * | 10/1941 | Cosgro | 15/229.11 |
| 2,811,299 A | * | 10/1957 | Swanson | 383/92 |
| 3,030,003 A | * | 4/1962 | Schanzle | 383/79 |
| 4,839,215 A | * | 6/1989 | Starling et al. | 428/131 |
| 5,016,859 A | * | 5/1991 | Zimmer et al. | 254/134.3 R |

(Continued)

FOREIGN PATENT DOCUMENTS

CN 1073148 A 6/1993
(Continued)

OTHER PUBLICATIONS

Hoxbro, Vivian, Domino Knitting, 2000, J.W. Cappelens Forlag, pp. 2, 3.*

(Continued)

*Primary Examiner* — Corrine M McDermott
*Assistant Examiner* — Alexander Orkin
(74) *Attorney, Agent, or Firm* — Knobbe, Martens, Olson & Bear, LLP

(57) ABSTRACT

The present invention relates to a tubular suture reinforcement material suitable for use in automatic suturing devices that are widely used in surgical operations, etc. More specifically, the present invention relates to a tubular suture reinforcement material with which a tubular shape is easily obtained to thereby increase its productivity, and removal of thread is easily achieved. The present invention provides a tubular suture reinforcement material for an automatic suturing device formed by stacking two sheet-like materials and sewing together both ends of the two sheet-like materials using two chain stitches (intralooping stitches) each thread end at each sewing end is suitably extended, and the thread end is passed through an anterior loop continuous to the thread end, thereby preventing the thread from unraveling.

12 Claims, 9 Drawing Sheets

U.S. PATENT DOCUMENTS

| | | | |
|---|---|---|---|
| 5,263,629 A | 11/1993 | Trumbull et al. | |
| 5,441,299 A | 8/1995 | Lauritzen et al. | |
| 5,503,638 A | 4/1996 | Cooper et al. | |
| 5,542,594 A | 8/1996 | McKean et al. | |
| 5,575,803 A | 11/1996 | Cooper et al. | |
| 5,766,188 A * | 6/1998 | Igaki | 606/151 |
| 5,814,057 A | 9/1998 | Oi et al. | |
| 5,843,096 A | 12/1998 | Igaki et al. | |
| 5,887,533 A * | 3/1999 | Tsukioka et al. | 112/65 |
| 6,063,097 A | 5/2000 | Oi et al. | |
| 6,273,897 B1 * | 8/2001 | Dalessandro et al. | 606/139 |
| 6,352,561 B1 * | 3/2002 | Leopold et al. | 623/1.23 |
| 6,551,350 B1 * | 4/2003 | Thornton et al. | 623/1.13 |
| 6,652,561 B1 * | 11/2003 | Tran | 606/232 |
| 6,984,242 B2 * | 1/2006 | Campbell et al. | 623/1.12 |
| 2004/0092963 A1 | 5/2004 | Moll et al. | |
| 2005/0118390 A1 * | 6/2005 | Wagner et al. | 428/102 |

FOREIGN PATENT DOCUMENTS

| | | |
|---|---|---|
| GB | 925286 | 5/1963 |
| GB | 983974 | 2/1965 |
| JP | 57-153682 A | 9/1982 |
| JP | 8-33641 | 2/1996 |
| JP | 08-033641 | 2/1996 |
| JP | 8-47526 | 2/1996 |
| JP | 1996-299427 | 11/1996 |
| JP | 9-24050 | 1/1997 |
| JP | 9-308635 | 12/1997 |
| JP | 2604025 | 4/2000 |
| JP | 2000-157622 | 6/2000 |
| JP | 2000-316963 | 11/2000 |
| JP | 3136392 | 12/2000 |
| JP | 2001-70433 | 3/2001 |
| JP | 3237749 | 10/2001 |
| JP | 3237750 | 10/2001 |
| JP | 2004-147902 | 5/2004 |
| WO | WO 02/076304 A1 | 10/2002 |

OTHER PUBLICATIONS

Tatsuo Adachi, "Sen'l Kogaku II Henso," Jikko Shuppan, 1973, pp. 38-39.

International Search Report dated Nov. 2, 2004 for International Application No. PCT/JP2004/010566.

"How to Bind Off Stitches", downloaded from "http://tlc.howstuffworks.com/home/how-to-knit6.htm".

* cited by examiner

SUTURE REINFOREMENT MATERIAL FOR AUTOMATIC SUTURING DEVICE

RELATED APPLICATIONS

This application is the U.S. National Phase under 35 U.S.C. 371 of International Application No. PCT/JP2004/010566, filed Jul. 16, 2004.

TECHNICAL FIELD

The present invention relates to a tubular suture reinforcement material suitable for use in automatic suturing devices that are widely used in surgical operations, etc. More specifically, the present invention relates to a tubular suture reinforcement material with which a tubular shape is easily obtained, productivity is high, and removal of thread is easily achieved.

BACKGROUND OF THE INVENTION

Hitherto, stapler-type automatic suturing devices containing a plurality of staples have been employed for suturing tissues. However, when such a suturing device is applied to pulmonary surgery, etc., air leakage may occur from the sutured area. In addition, when applied to soft tissues, problems of tissue damage or tear may arise.

In order to solve the above problems, the applicant has already filed previous applications relating to tubular suture reinforcement materials to be fitted to a staple part of the suturing device, thereby preventing air leakage from the sutured area, reinforcing the area, etc. (e.g., Japanese Registered Utility Model No. 2604025; Japanese Patent Nos. 3136392, 3237749, and 3237750; Japanese Unexamined Patent Publication Nos. 1997-24050, 1997-308635, 2000-157622, 2000-316963, and 2001-70433).

As other applicants' applications relating to tubular suture reinforcement materials, Japanese Patent No. 3040930 and Japanese Unexamined Patent Publication No. 1996-299427 can be mentioned.

The above-mentioned applications disclose a structure wherein a sheet-like material, such as a nonwoven fabric or film made of a biodegradable and bioabsorbable material, is formed into a tubular shape, or a structure wherein a nonwoven fabric made of a biodegradable and bioabsorbable material and a stretchable fabric are integrally combined to form a tubular shape. The tubular shape is obtained, for example, by a method for temporarily adhering both ends (both edges) of stacked sheet-like materials and a method for basting both ends thereof using rough stitches. More specifically, a running stitch in which the front and back sides of stacked sheet-like materials are stitched in turn can be mentioned as an example.

Temporary adhesion or basting of the sheet-like material as described above are conducted for the purpose of easily separating a suture reinforcement material that is to be removed with a lesion from a suture reinforcement material that is to be left in a human body, when the lesion is removed from the human body after the affected region has been sutured and the lesion is cut off from normal tissues using an automatic suturing device equipped with a suture reinforcement material.

However, the tubular suture reinforcement material manufactured using temporary adhesion is disadvantageous in that sheet-like materials joined by adhesion tend to separate from each other, and the tubular suture reinforcement material manufactured using a running stitch is disadvantageous in that the sewing manner requires a lot of time and skill, and removal of thread is difficult depending on the kind of sheet-like material, sewing pitch, etc.

SUMMARY OF THE INVENTION

The invention aims to overcome the above-described drawbacks. The invention provides a novel suture reinforcement material for an automatic suturing device that can be manufactured without requiring advanced skill and from which a thread can be very smoothly removed irrespective of the kind of material used and the sewing pitch of the suture reinforcement material.

The invention has the following characteristic structures.

Item 1. A tubular suture reinforcement material for an automatic suturing device, wherein both ends of one or two sheet-like materials are sewed using a chain stitch (intralooping stitch) with a single thread to form a tubular shape, and one or two thread ends at one or two sewing ends are suitably extended.

Item 2. A tubular suture reinforcement material for an automatic suturing device according to Item 1, wherein the tip part of the suture reinforcement material is sewed in a tapering manner or sewed into a bag-like shape.

Item 3. A tubular suture reinforcement material for an automatic suturing device according to Item 1 or 2, wherein at least one portion of the sheet-like material is made of at least one member selected from the group consisting of knitted materials, woven materials, nonwoven fabrics, and film, the at least one member being made of a biodegradable and bioabsorbable material.

Item 4. A tubular suture reinforcement material for an automatic suturing device according to Item 1, wherein the sheet-like material and a stretchable knitted material or woven material are stacked into a tubular shape.

Item 5. A tubular suture reinforcement material for an automatic suturing device according to any one of Items 1 to 4, wherein a projection is formed on the sewing end portion of the one or two sheet-like materials forming the tubular shape.

Item 6. A tubular suture reinforcement material for an automatic suturing device according to any one of Items 1 to 4, wherein extended thread ends at the sewing end are tied in a ring shape.

Item 7. A tubular suture reinforcement material for an automatic suturing device according to any one of Items 1 to 4, wherein a stopper is passed through a loop on a side of the extended thread end, thereby preventing a thread from unraveling.

Item 8. A tubular suture reinforcement material for an automatic suturing device according to any one of Items 1 to 4, wherein the extended thread end is passed through an anterior loop continuous to the thread end, thereby preventing a thread from unraveling.

Item 9. A tubular suture reinforcement material for an automatic suturing device according to any one of Items 1 to 4, wherein a loop on a side of the sewing end is tied to a loop immediately before the loop, thereby preventing a thread from unraveling.

Item 10. A method for manufacturing a tubular suture reinforcement material for an automatic suturing device comprising: sewing both ends of one or two sheet-like materials using a chain stitch (intralooping stitch) with a single thread to give a tubular suture reinforcement material, and suitably extending one or two thread ends at one or two sewing ends.

Item 11. An automatic suturing device, comprising a cartridge containing staples and a frame equipped with a staple receiving slot, wherein a tubular suture reinforcement material for an automatic suturing device according to any one of Items 1 to 9 is fitted to the cartridge and/or the frame.

DESCRIPTION OF THE REFERENCE NUMERALS

Figure 1:
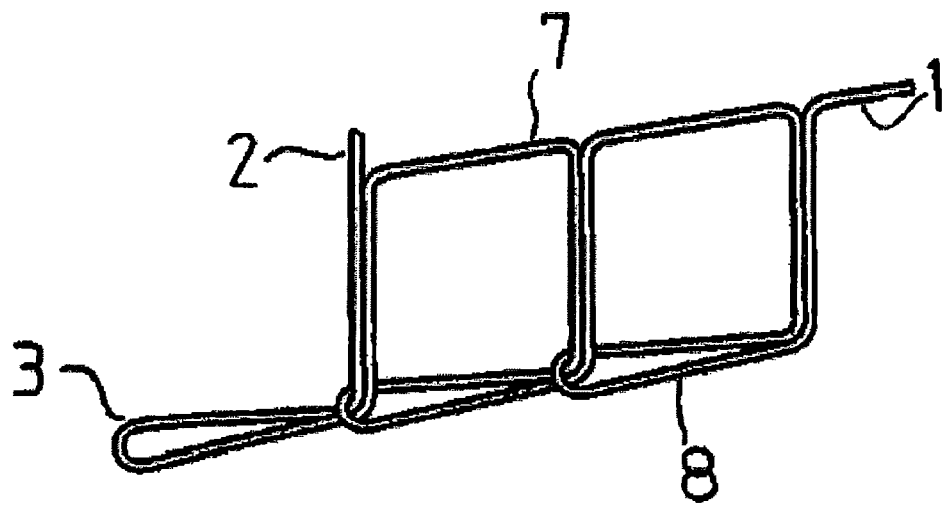
FIG. 1 schematically shows a stitching style of the invention.

In FIGS. 1 to 16, reference numerals denote as follows: 1, thread end at sewing start; 2, thread end at sewing end; 3, loop; 4, tubular suture reinforcement material; 5, biodegradable and bioabsorbable nonwoven fabric; 6, powernet fabric (stretchable fabric); 7, stitches on the front side; 8, stitches on the back side; 9, stopper; 10, automatic suturing device; 11, cartridge; 12, frame; 13, knot; 14, projection; and 15, knot.

DETAILED DESCRIPTION OF THE INVENTION

Hereinafter, the invention will be described in detail.

A sheet-like material of the invention is made of a material suitably selected from nonbioabsorbable materials, such as polyamide, polyester, silicone, fluororesin, etc., and biodegradable and bioabsorbable materials, such as polyglycolic acid, polylactic acid, a copolymer of glycolic acid and lactic acid, a copolymer of glycolic acid and caprolacton, a copolymer of glycolic acid and caprolacton, or a mixture thereof, polyparadioxanone, polycaprolactone, chitin, animal tissues, and the like. Examples of formations of the sheet-like material include a knitted material, a woven material, a nonwoven fabric, a film, a sheet, a sponge sheet, etc., made of the above-mentioned nonbioabsorbable materials and/or biodegradable and bioabsorbable materials.

Particularly preferable materials include nonwoven fabrics made of polyglycolic acid, which is excellent in flexibility, breathability, rigidity, thickness, blood absorbing properties, ease of staple penetration, and hydrolyzability. Such nonwoven fabrics can be prepared by a suitable method, such as a needle punching method, a meltblown method, or the like.

The suture reinforcement material of the invention is formed into a tubular shape by sewing both ends of one sheet-like material after the one sheet-like material is folded or by stacking two sheet-like materials, and then sewing both ends of the stacked sheet-like materials. When two sheet-like materials are stacked to form a tubular material, one of the two sheet-like materials may be a stretchable material. Preferable examples of such stretchable sheet-like materials include knitted or woven materials with stretchability in lengthwise and/or crosswise directions, in which rubber threads, polyurethane-based elastic threads, crimped threads, and bulky yarns, etc. are suitably interknitted or interwoven. A suture reinforcement material prepared by combining a stretchable material with a non-stretchable material facilitates fitting of the suture reinforcement material to an automatic suturing device, adjustment (position correction) after fitting, etc., and thus is preferable.

Although there is no limitation to the mode of knitting or weaving of the stretchable sheet-like material, a powernet fabric produced by warp knitting stretchable threads obtained by covering polyurethane threads by nylon threads is preferable in view of easy cutting, easy sewing during formation of a tubular material, shape stability, etc.

In the case of using one sheet-like material, the tubular material can be obtained by sewing together both ends of one sheet-like material that is cut according to the outer surface dimensions of a suturing device, after the one sheet-like material is folded. Alternatively, in the case of using two sheet-like materials, the tubular material can be obtained by stacking them, and then sewing together both ends of the sheet-like materials.

The term "tubular" used herein denotes that both ends of a sheet-like material are joined together, and a tubular shape may be a cylinder, a prism, or a plane.

The sewing methods for obtaining the tubular shape can be suitably selected from the method for sewing both ends of the sheet-like material(s) in parallel, the method for sewing the tip part thereof in a tapering manner, or the method for sewing the tip part thereof in a bag-like manner, etc. The tapered or bag-like tip part is advantageous in that the tubular material can be easily fitted to a suturing device.

Although any threads used for sewing clothes can be generally used for sewing both ends, biodegradable and bioabsorbable surgical sutures, such as those made of polyglycolic acid, a copolymer of glycolic acid and lactic acid, a copolymer of lactic acid and caprolacton, etc., are preferable. This is because the suture reinforcement material is for use in medical applications, and the material might be erroneously left in the human body.

The invention is characterized by the use of a chain stitch (intralooping stitch) with a single thread as a stitching style.

The chain stitch (intralooping stitch) with a single thread creates stitches in which loops are formed with a single thread.

Specific examples of stitching styles of the invention are shown in FIGS. 1 to 7, but the invention is not limited thereto. The term "needle-insertion side" used in the following denotes the needle-insertion side of the stacked sheet-like materials, i.e., the upper side as viewed in the figures, and the term "rear side" denotes the side opposite to the needle-insertion side of the stacked sheet-like materials, i.e., the bottom side as viewed in the figures. In FIGS. 1 to 6, the stacked sheet-like materials are not illustrated.

FIG. 1 shows that a loop 3 passes through the stacked sheet-like materials from the needle-insertion side, and then is secured by intralooping with a succeeding loop on the rear side of the stacked sheet-like materials. In the invention, the "chain stitch (intralooping stitch)" denotes that a loop of thread passes through another loop formed by the same thread.

Figure 2:
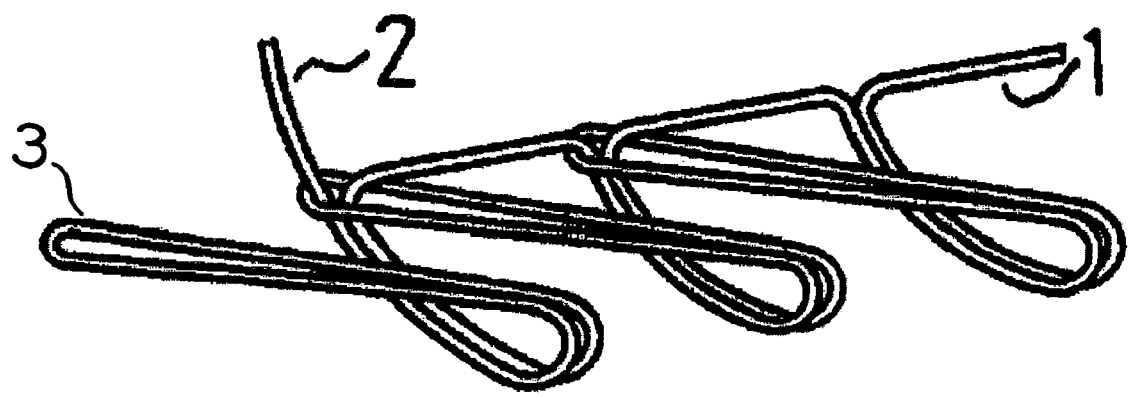
FIG. 2 schematically shows a stitching style of the invention.

FIG. 2 shows that a loop 3 passes into the stacked sheet-like materials from the needle-insertion side, appears on the needle-insertion side through a part of the stacked sheet-like materials, and then is secured by intralooping with a succeeding loop at the following needle-penetration point. Hereinafter, the phrase "appearing on the needle-insertion side after passing through a part of the sheet-like material" includes the case where a loop appears on the needle-insertion side passing across the end surface of the stacked sheet-like materials, the case where a loop appears on the needle-insertion side penetrating the sheet-like materials, etc.

Figure 3:
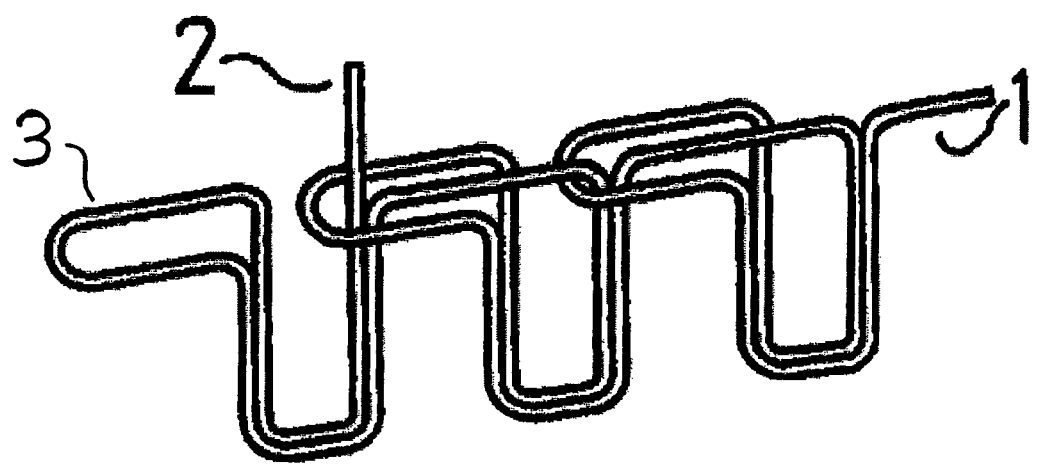
FIG. 3 schematically shows a stitching style of the invention.

FIG. 3 shows that a loop 3 passes through the stacked sheet-like materials from the needle-insertion side, goes slightly ahead, passes through the stacked sheet-like materials to appear on the needle-insertion side, and then is secured by intralooping with a succeeding loop at the next needle-penetration point on the needle-insertion side of the sheet-like material.

Figure 4:
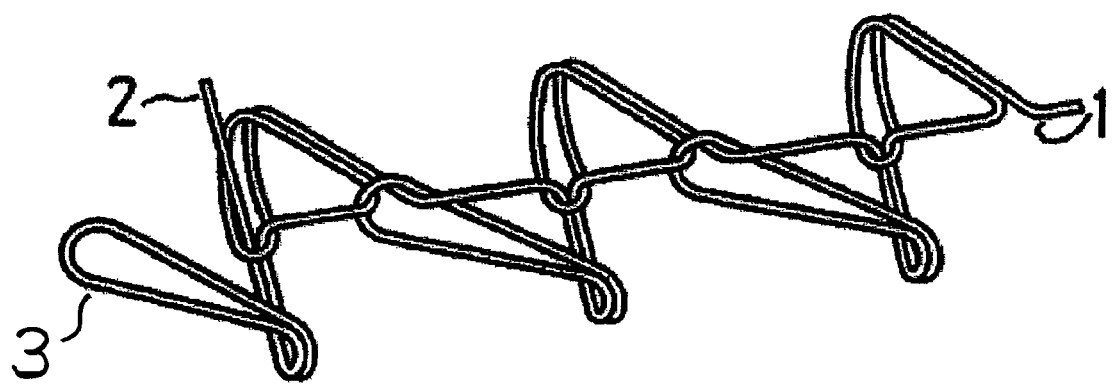
FIG. 4 schematically shows a stitching style of the invention.

FIG. 4 shows that a loop 3 enters the stacked sheet-like materials from the needle-insertion side, passes through a part of the stacked sheet-like materials to appear on the needle-insertion side, and then is secured by intralooping with a succeeding loop at the next needle-penetration point on a stitch formation line (sewed line).

Figure 5:
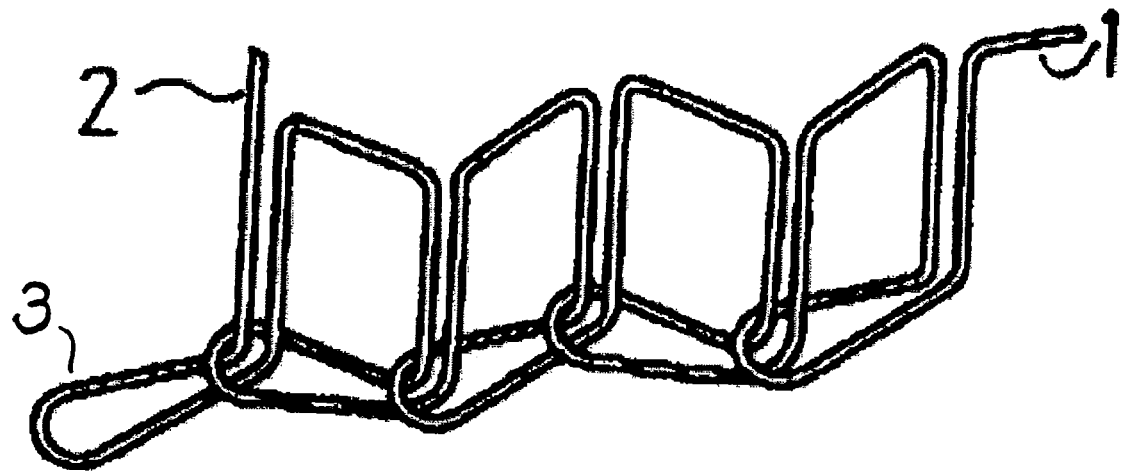
FIG. 5 schematically shows a stitching style of the invention.

FIG. 5 shows a modified example of the stitching style of FIG. 1, forming a zigzag pattern.

Figure 6:
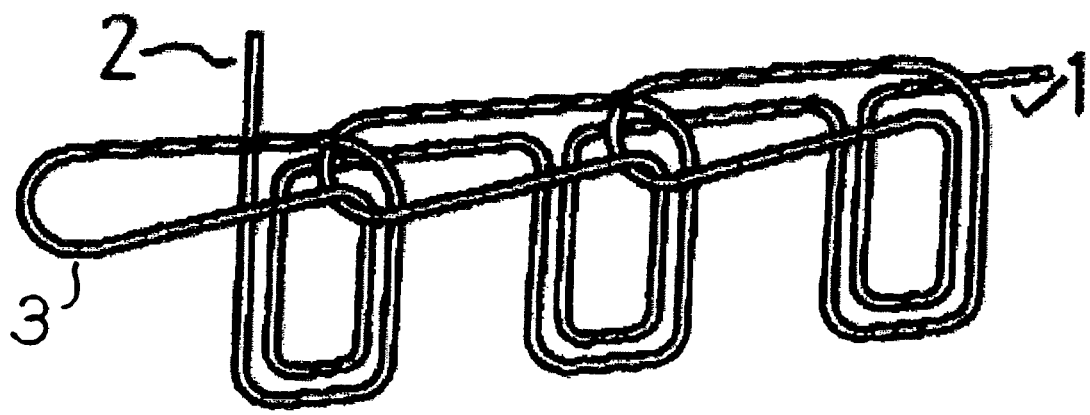
FIG. 6 schematically shows a stitching style of the invention.

FIG. 6 shows that a loop 3 passes through to appear on the rear side of the stacked sheet-like materials from the needle-insertion side, goes slightly back, passes through the stacked sheet-like materials to appear on the needle-insertion side, and then the loop 3 is secured by intralooping with a succeeding loop 3 which passes through the stacked sheet-like materials.

Figure 7:
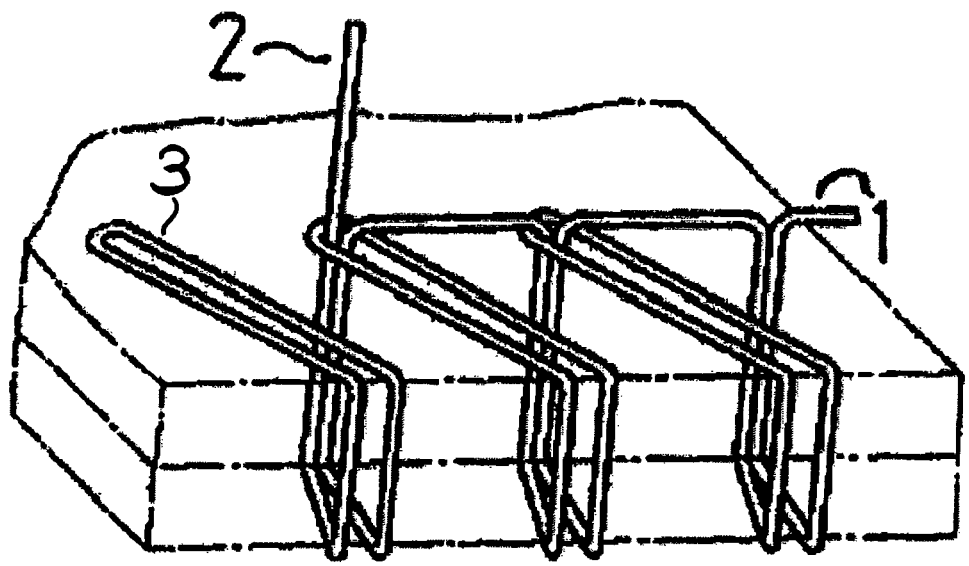
FIG. 7 schematically shows a stitching style of the invention.

FIG. 7 shows that a loop 3 goes through the stacked sheet-like materials and a loop that has already passed across the stacked sheet-like materials to appear on the needle-insertion side of the stacked sheet-like materials, and further the loop passing through is extended to the next needle-penetration point across the end surface of the stacked sheet-like materials.

In each figure, the reference numeral 1 denotes a thread end at the sewing start, and the reference numeral 2 denotes a thread end at the sewing end. In FIG. 1, the reference numerals denote as follows: 3, a loop; 7, stitches on the front side, and 8, stitches on the back side.

Each example above shows a chain stitch (intralooping stitch) made by a single thread. In the chain stitch (intralooping stitch), by pulling the thread end(s) 2 at the sewing end(s), the thread(s) is removed from the formed loops, and thus the sewed seams are smoothly unstitched. Such sewing can be done by hand, and as a matter of fact, a commercially-available sewing machine can also be used. In the latter case, sewing can be done very efficiently.

It is preferable to extend the thread end by a suitable length so that a part of the suture reinforcement material to be removed with the lesion (e.g., powernet fabric) can be easily separated from a part of the suture reinforcement material to be left in the human body (for example, a biodegradable and bioabsorbable material). The extended thread ends at the sewing ends may be tied in the shape of a ring. As another example, the thread end(s) at the sewing start(s) may be tied to the sheet-like material (e.g., powernet fabric), and the extended thread ends at the sewing ends may be tied in the shape of a ring (annular). In this case, the thread can be very easily removed, and the sheet-like material (e.g., powernet fabric) can be easily removed with the sewing thread after a surgical operation.

In order to prevent the thread from being unintentionally drawn out from the suture reinforcement material, a stopper may be provided in a loop on the side of the thread end(s) at the sewing end(s), the thread end(s) may be passed through the anterior loop continuous to the thread end(s) at the sewing end(s), or the loop on the side of the sewing end(s) may be passed through the immediately anterior loop, and may be tied by a single knot.

Automatic suturing devices to which the suture reinforcement material of the invention can be applied include MULTIFIRE GIA80, MULTIFIRE GIA60, MULTIFIRE GIA50, and MULTIFIRE GIA90P (manufactured by U.S. SURGICAL), PROXIMATE LINEAR CUTTER 55 mm and PROXIMATE LINEAR CUTTER 75 mm (manufactured by Ethicon Endo-Surgery), ENDO GIA(2)30, ENDO GIA(2)45, and ENDO GIA(2)60 (manufactured by U.S. SURGICAL), and ENDOPATH END CUTTER ETS45 and ENDOPATH END CUTTER ETS EZ45 (manufactured by Ethicon Endo-Surgery).

The suture reinforcement material of the invention is applied to a suturing device by encapsulating (fitting) it in both or either of a cartridge containing a staple and/or a frame having a staple receiving slot.

In this case, to simplify the fitting of the tubular suture reinforcement material to an automatic suturing device, the sewing end portion(s) of the sheet-like material(s) forming the tubular suture reinforcement material can be extended to form a projection.

BEST MODE FOR CARRYING OUT THE INVENTION

Hereinafter, the suture reinforcement material of the invention will be described with reference to the drawings, but is not limited thereto.

Embodiment 1

Figure 8:
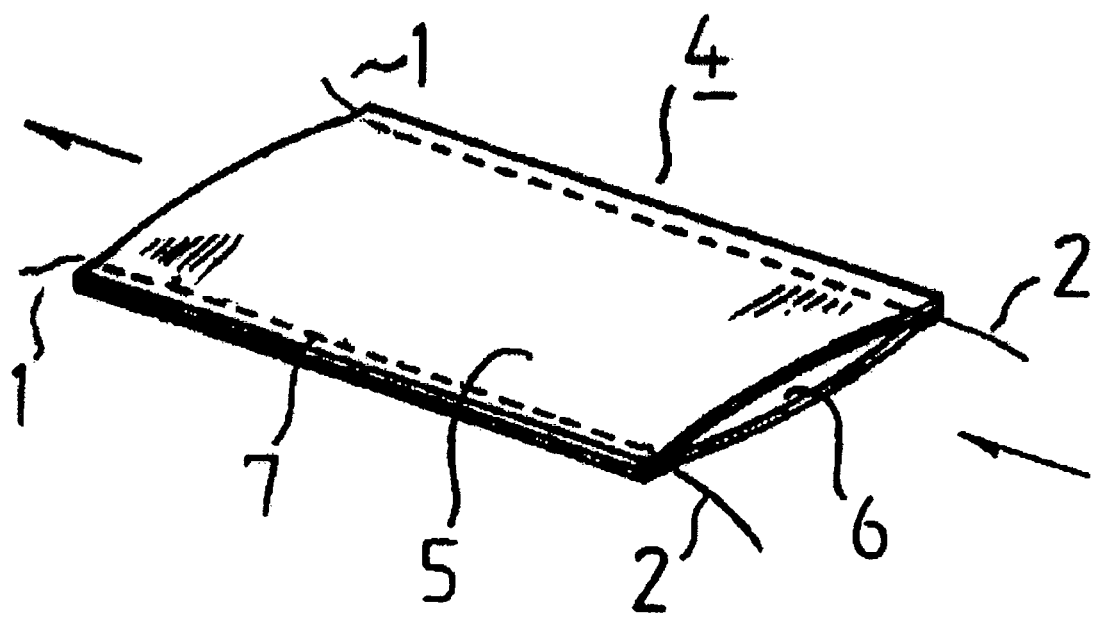
FIG. 8 is a perspective view showing a structure of a suture reinforcement material according to one embodiment of the invention.
Figure 9:
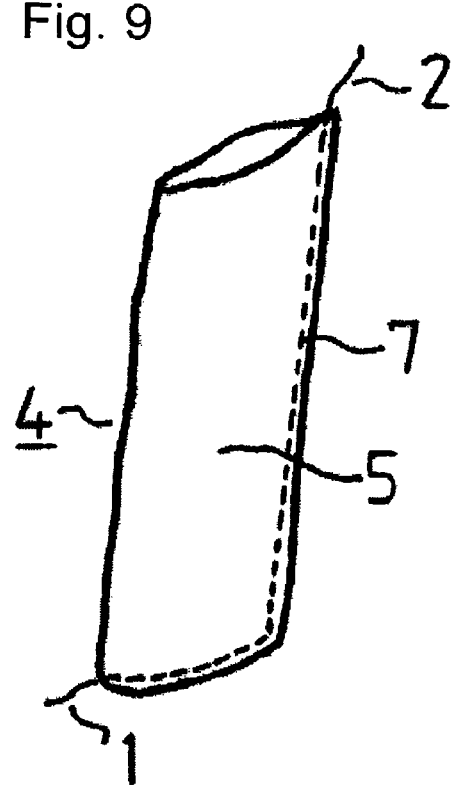
FIG. 9 is a perspective view showing a structure of a suture reinforcement material according to another embodiment of the invention.

FIGS. 8 and 9 show the suture reinforcement material of the invention manufactured by the stitching style shown in FIG. 1. FIG. 8 is a tubular suture reinforcement material 4 that is prepared by stacking a biodegradable and bioabsorbable nonwoven fabric 5 and a stretchable powernet 6, and sewing together both ends of the stacked materials with a DH-type chain stitching machine manufactured by Pegasus. FIG. 9 shows a bag-like tubular suture reinforcement material 4 whose tip part is closed. The bag-like tubular suture reinforcement material is obtained by folding one sheet of the nonwoven fabric 5, stacking both ends, and sewing them in a tubular shape with the same sewing machine as described above.

Although not illustrated, as a modified example of FIG. 8, a suture reinforcement material whose tip part is sewed in a tapering manner can also be mentioned.

In either case, the thread end(s) 2 at the sewing end(s) are suitably extended for easy removal of thread.

Figure 10:
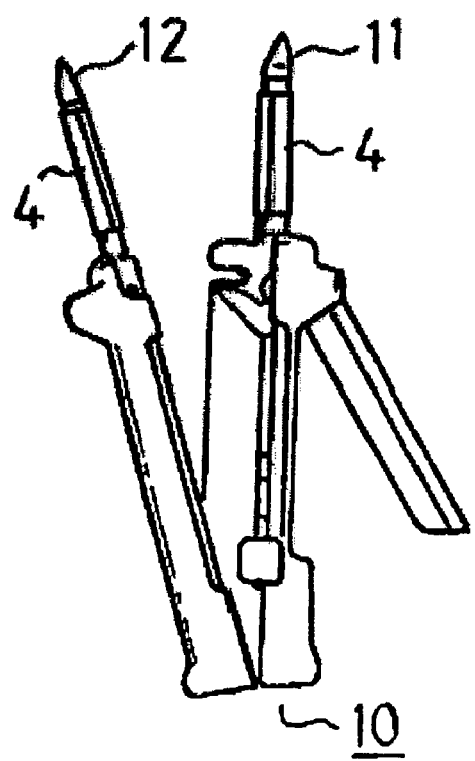
FIG. 10 is a front view showing an automatic suturing device equipped with the suture reinforcement material of the invention.
Figure 11:
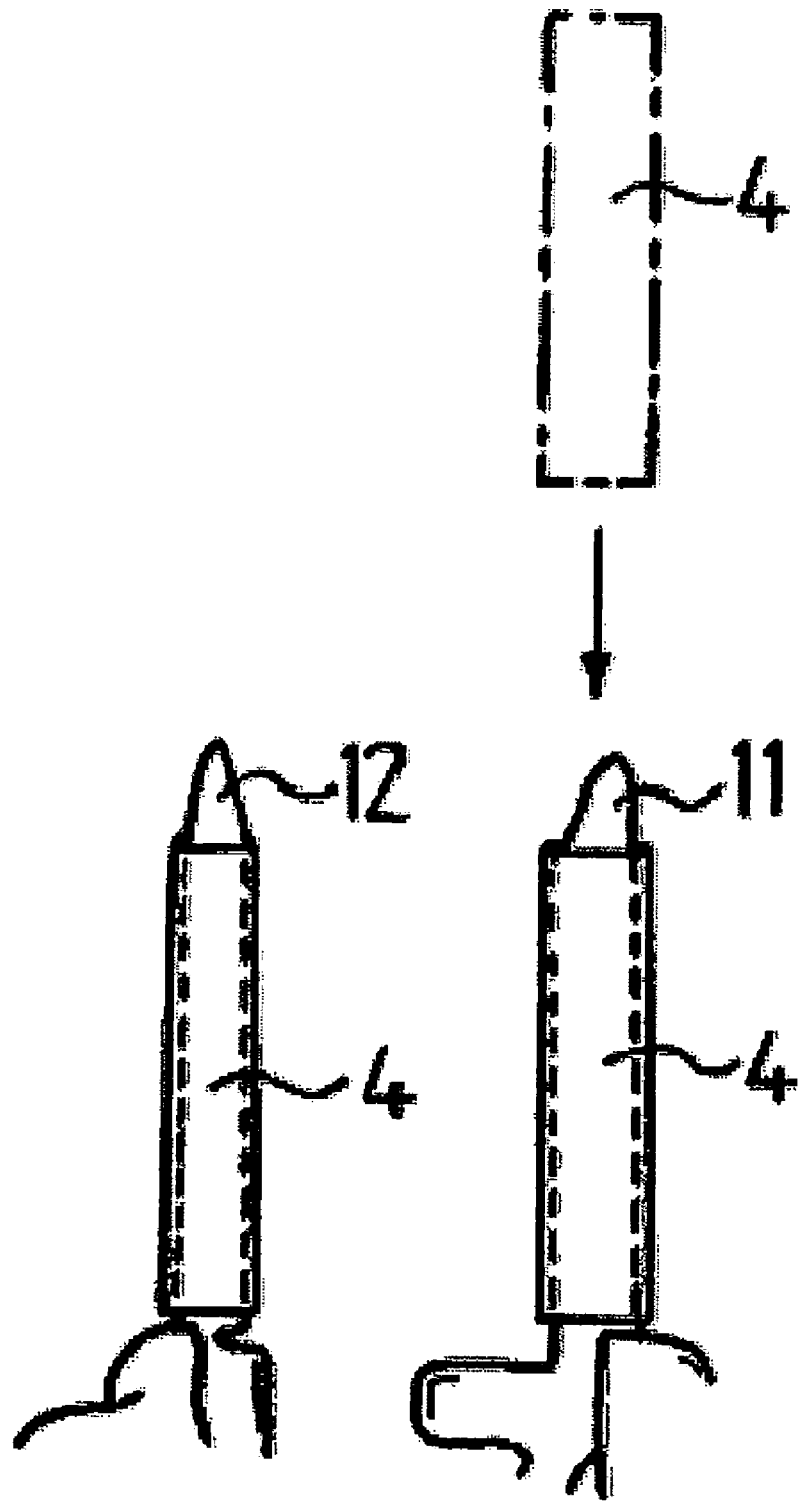
FIG. 11 is a partially enlarged front view showing the process of fitting the suture reinforcement material of the invention of FIG. 10 to an automatic suturing device.

Two pieces of the suture reinforcement material 4 thus obtained are individually fitted to a cartridge 11 containing staples and a frame 12 of the automatic suturing device 10 of FIG. 10 for use, as shown in an enlarged view of FIG. 11. The suture reinforcement material is fitted to the automatic suturing device 10 in such a manner that the extended thread end 2 at the sewing end is placed frontward, i.e., at the gripping part of the automatic suturing device 10.

Embodiment 2

Figure 12:
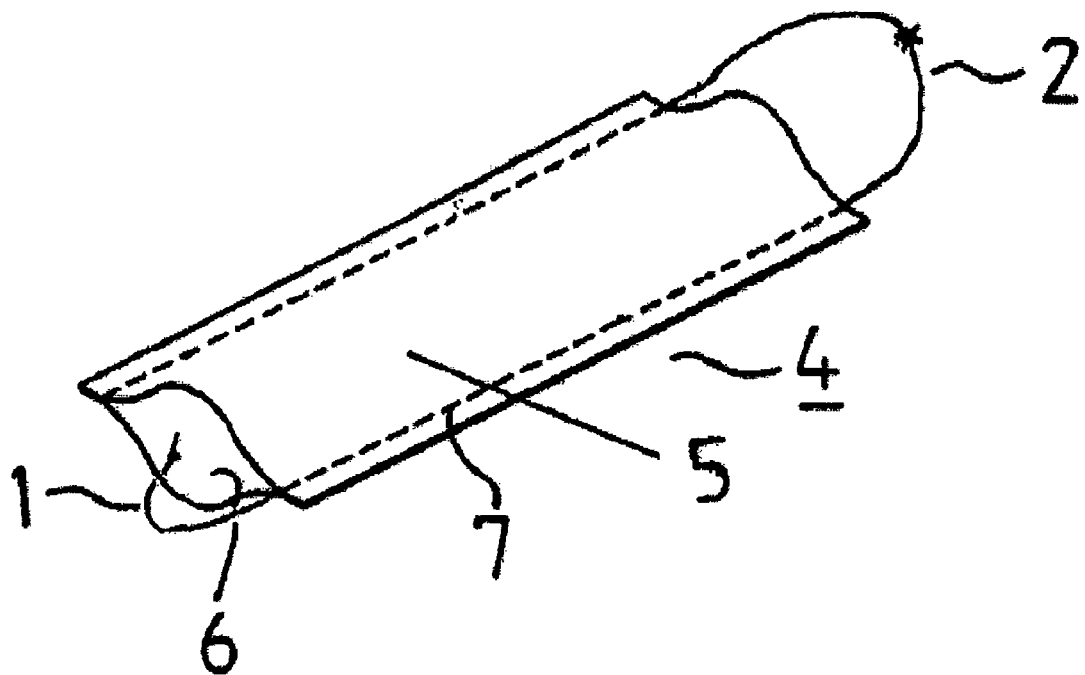
FIG. 12 is a perspective view showing a structure of a suture reinforcement material according to another embodiment of the invention.

FIG. 12 shows a structure of a suture reinforcement material according to another embodiment. The suture reinforcement material is a tubular suture reinforcement material, which is obtained by stacking a biodegradable and bioabsorbable nonwoven fabric 5 and a stretchable powernet fabric 6, and sewing both ends. The thread end 1 at the sewing start is joined to the powernet fabric 6 and the thread ends 2 at the both sewing ends are tied to form a ring (annular).

This structure with the ring-shaped thread end 2 at the sewing end facilitates the handling of the material and the removal of the thread. Further, since the thread end 1 at the sewing start is tied to the powernet material 6, the power net material is easily removed with the thread after a surgical operation.

Embodiment 3

Figure 13:
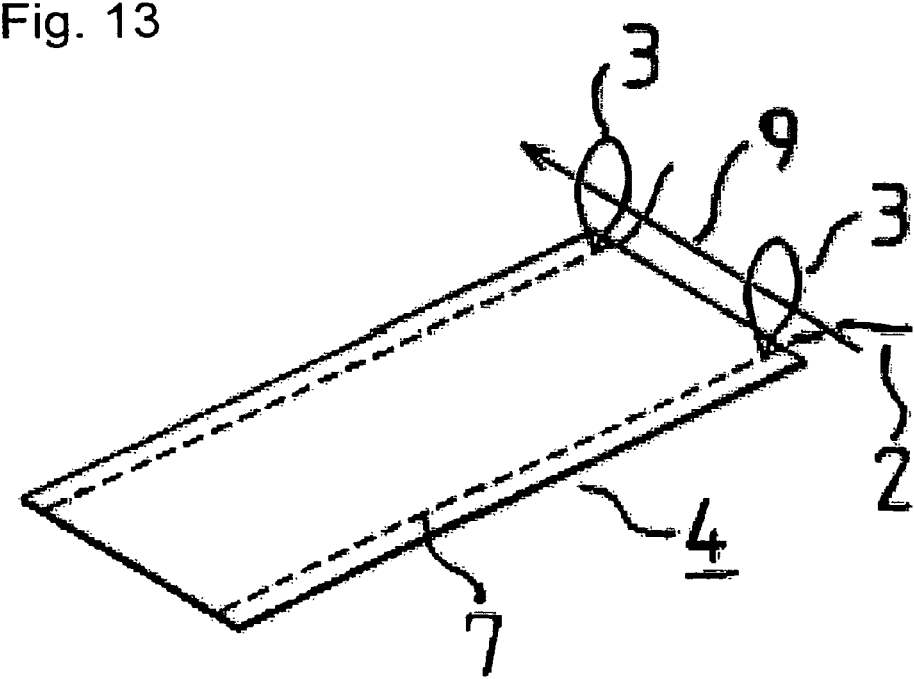
FIG. 13 is a perspective view showing an example of a suture reinforcement material which prevents the removal of thread end(s) of the invention.
Figure 14:
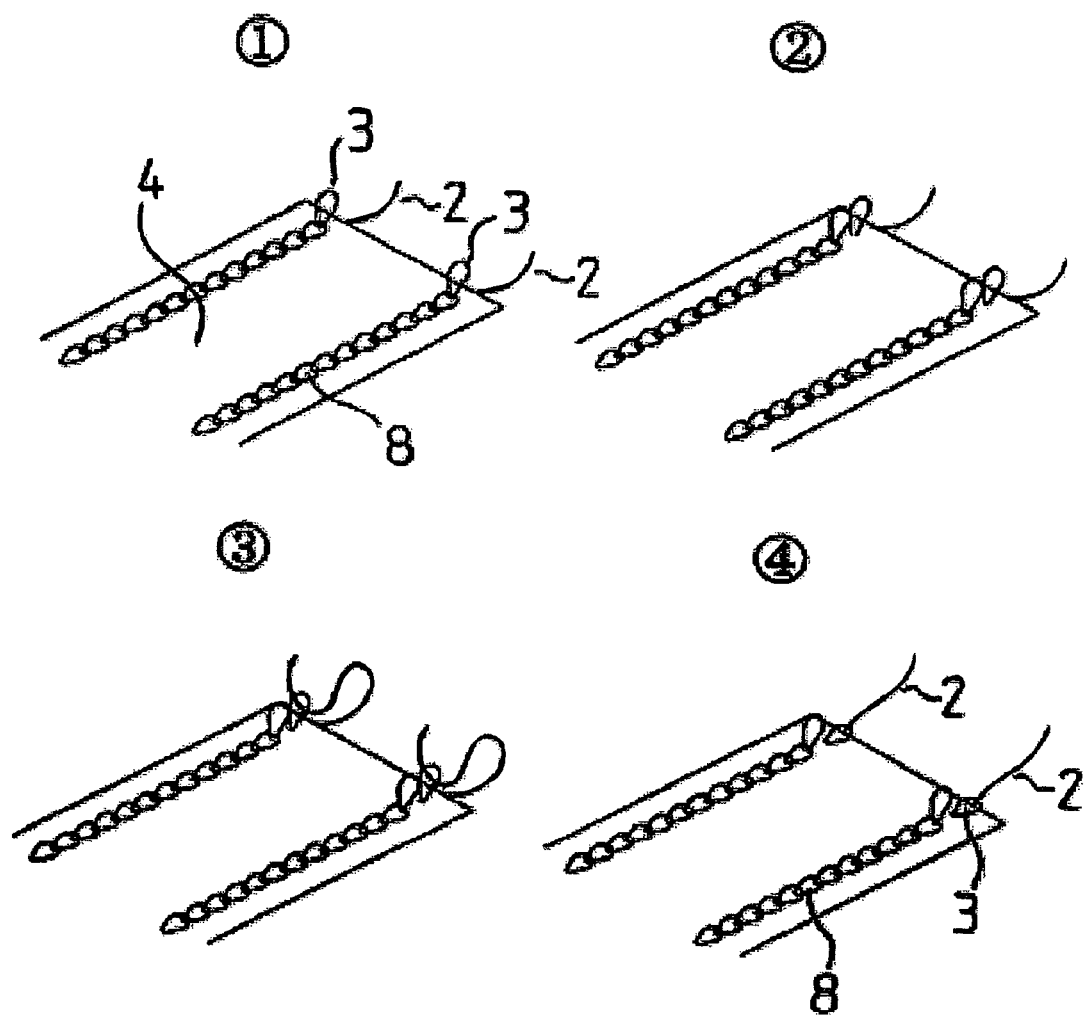
FIG. 14 is a perspective view showing another example of a suture reinforcement material which prevents the removal of thread end(s) of the invention.

FIGS. 13 and 14 each show another suture reinforcement material according to another embodiment that is structured to prevent the thread ends 2 at the sewing ends from unraveling.

FIG. 13 shows that a stopper 9 passes through loops 3 of the thread ends 2 at the sewing end. The stopper 9 may be thread, finely-cut material or film, etc., and materials other than a fiber may be used. A suitably rigid material that can easily be passed through the loop and drawn out from the loop is preferable.

FIG. 14 shows a suture reinforcement material in which the thread ends 2 at the sewing ends are passed through the anterior loops 3 continuous to the thread ends 2, thereby preventing the thread ends 2 at the sewing ends from unraveling as described above. The thread end 2 is passed through the loop 3 by the following steps 1 to 4 as shown in the figure. The thread ends 2 at the sewing ends are passed through the loop 3, and finally, the thread ends 2 are pulled to secure it.

These methods for preventing the thread from unraveling keep the thread from being drawn out from the suture reinforcement material due to any tension that is unintentionally applied to the thread end 2. Accordingly, after the predetermined suturing process is complete, the thread is drawn out from the loop 3 by removing the stopper, returning the thread end passing through the loop 3 to the original position, or pulling the thread.

Figure 15:
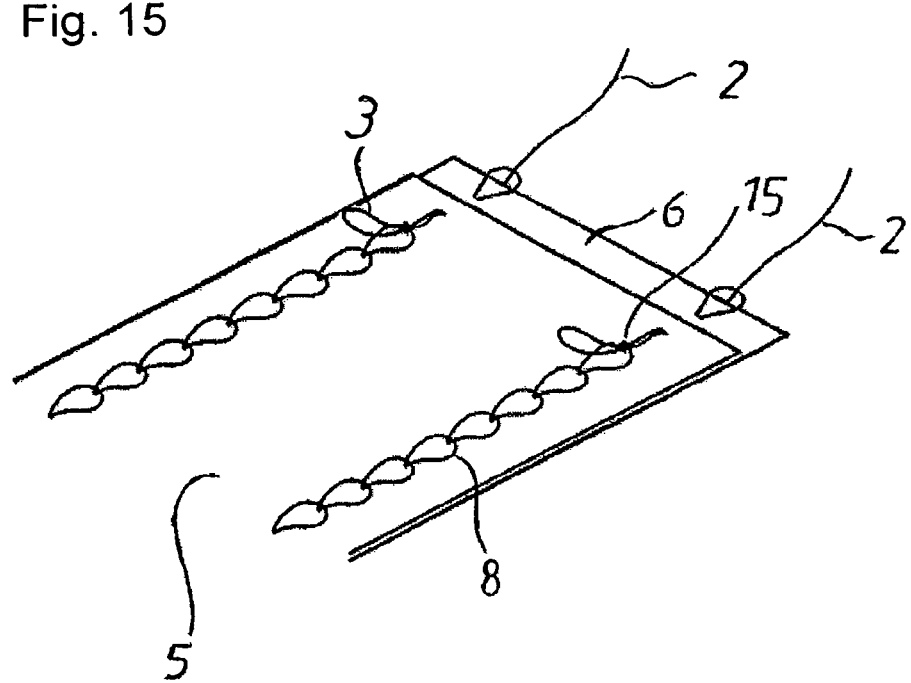
FIG. 15 is a perspective view showing another example of a suture reinforcement material which prevents the removal of thread end(s) of the invention.

FIG. 15 shows another method for preventing a thread from unraveling.

In the structure, the loop 3 at the sewing end is passed through a loop immediately before the loop 3 and is fixed by a single knot 15, thereby preventing the loop 3 from being drawn out from the sheet. More specifically, this structure can prevent the seam from unraveling, which is caused by tension applied when the material is fitted to a cartridge or a frame. After the suturing is complete, the edge of the biodegradable and bioabsorbable nonwoven fabric 5 is torn by pulling the thread end, and subsequently the seam is unraveled. Thus, the powernet material 6 can be easily removed together with the sewing thread.

Any methods for preventing threads from unraveling can be employed in addition to the above methods. For example, a thread end can be temporarily adhered to a sheet-like material by applying adhesive to the sheet-like material, or a thread end can be temporarily fixed to a sheet-like material by adhesive tape, etc.

Embodiment 4

Figure 16:
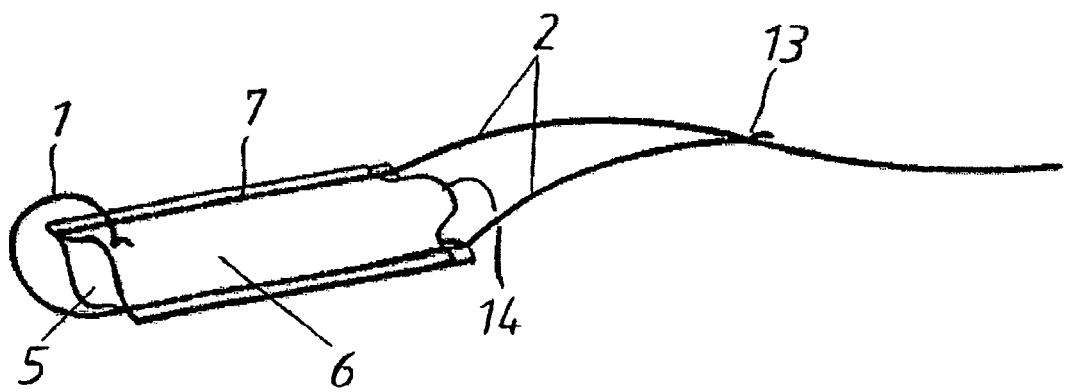
FIG. 16 is a perspective view showing one structure of a suture reinforcement material of the invention in which a projection is formed.

FIG. 16 shows a structure of a tubular suture reinforcement material which can be easily fitted to an automatic suturing device. More specifically, the sewing end portion of sheet-like materials forming the tubular suture reinforcement material is extended to form a projection 14. In this example, the sewing end portion of the powernet fabric 6 is cut in a convex shape to form the projection 14. By pulling the projection 14, the tubular suture reinforcement material can be easily fitted to an automatic suturing device.

The projection 14 may be suitably formed into any shape and set to any dimensions considering its operability. Any method can be employed for forming a projection to the powernet fabric 6, in addition to cutting the material as described above. For example, such projection may be formed by adhering or sewing other materials, such as cloth, film, etc. The projection may be formed on a side of the biodegradable and bioabsorbable nonwoven fabric 5 side or on both sides of the nonwoven fabric 5 and the powernet material 6.

EFFECT OF THE INVENTION

In the suture reinforcement material of the invention, a seam can be easily formed with an already-existing sewing machine, etc. Therefore, a tubular suture reinforcement material can be manufactured without requiring skill, and further the productivity is high and there are no variations in quality. As compared with stitches made by the conventional running stitch, a thread is smoothly removed, and a sheet-like material can be separated with no difficulties after a surgical operation. Further, the suture reinforcement material of the invention can be easily fitted to an automatic suturing device and the unraveling of threads can be prevented during the process.

The invention claimed is:

1. A tubular suture reinforcement material for an automatic suturing device,
   wherein the tubular suture reinforcement material is formed by stacking two sheet-like materials and sewing together both ends of the two sheet-like materials using two chain stitches,
   wherein said chain stitches comprise a plurality of loops in which one of said loops passes through an adjacent loop in a direction away from a sewing end, thereby providing intralooping stitches,
   wherein, at the sewing end, a loop next to the sewing end does not pass through another loop anterior to the loop next to the sewing end, and
   wherein a thread end at the sewing end passes through the loop next to the sewing end, which is continuous to the thread end, thereby preventing the thread from unraveling without tying a knot at the sewing end and is returned to the sewing end after passing through the loop next to the sewing end.

2. A tubular suture reinforcement material for an automatic suturing device according to claim 1, wherein the tip part of the suture reinforcement material is sewed in a tapering manner or sewed into a bag-like shape.

3. A tubular suture reinforcement material for an automatic suturing device according to claim 1, wherein at least one portion of the sheet-like material is made of at least one member selected from the group consisting of knitted materials, woven materials, nonwoven fabrics, and film, the at least one member being made of a biodegradable and bioabsorbable material.

4. A tubular suture reinforcement material for an automatic suturing device according to claim 1, wherein the sheet-like material and a stretchable knitted material or woven material are stacked into a tubular shape.

5. A tubular suture reinforcement material for an automatic suturing device according to claim 1, wherein a projection is formed on the sewing end portion of the one or two sheet-like materials forming the tubular shape.

6. A tubular suture reinforcement material for an automatic suturing device according to claim 1, wherein extended thread ends at the sewing end are tied in the shape of a loop.

7. An automatic suturing device, comprising a cartridge containing staples and a frame equipped with a staple receiving slot, wherein a tubular suture reinforcement material for an automatic suturing device according to claim 1 is fitted to the cartridge and/or the frame.

8. A tubular suture reinforcement material for an automatic suturing device according to claim 1, wherein a loop on a side of the sewing end is tied to a loop immediately before the loop, thereby preventing a thread from unraveling.

9. A method for removing a lesion from an affected region of a patient,
   suturing said affected region with a tubular suture reinforcement material according to claim 1,
   cutting off the lesion from normal tissue in the affected region, and
   removing said lesion along with a part of said suture reinforcement material while leaving another part of said suture reinforcement material in the patient.

10. The method according to claim 9, wherein the affected region comprises a soft tissue.

11. The method according to claim 10, wherein the affected region comprises pulmonary tissue.

12. A method for manufacturing a tubular suture reinforcement material for an automatic suturing device comprising:
   stacking two sheet-like materials,
   sewing together both ends of the two sheet-like materials using two chain stitches, wherein said chain stitches comprise a plurality of loops in which one of said loops passes through an adjacent loop in a direction away from a sewing end, thereby providing intralooping stitches, said intralooping stitches suitably extending each thread end at each sewing end,
   at the sewing end, having a loop next to the sewing end not pass through another loop anterior to the loop next to the sewing end, and
   passing the thread end at the sewing end through the loop next to the sewing end, which is continuous to the thread end without tying a knot at the sewing end, wherein the thread end is returned to the sewing end after passing through the loop next to the sewing end.

* * * * *

UNITED STATES PATENT AND TRADEMARK OFFICE
CERTIFICATE OF CORRECTION

PATENT NO.       : 8,177,797 B2                                      Page 1 of 1
APPLICATION NO.  : 10/564874
DATED            : May 15, 2012
INVENTOR(S)      : Shimoji et al.

It is certified that error appears in the above-identified patent and that said Letters Patent is hereby corrected as shown below:

Page 1 (item 54) and column 1 at line 1 (title), Change "REINFOREMENT" to --REINFORCEMENT--.

Page 1 (item 57) Abstract at line 12, Change "stitches)" to --stitches),--.

In column 4 at line 1, Change "caprolacton," to --caprolactone,--.

In column 4 at line 2, Change "caprolacton," to --caprolactone,--.

In column 4 at line 62, Change "caprolacton," to --caprolactone,--.

Signed and Sealed this
Sixth Day of November, 2012

David J. Kappos
*Director of the United States Patent and Trademark Office*